United States Patent
Han (10) Patent No.: US 7,245,372 B2
(45) Date of Patent: Jul. 17, 2007

(54) OPTICAL ANALYZER FOR IMPROVING RESOLUTION OF A TIME-VARYING SPECTRUM AND METHOD THEREFOR

(75) Inventor: Wan-taek Han, Hwaseong-si (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 302 days.

(21) Appl. No.: 10/982,814

(22) Filed: Nov. 8, 2004

(65) Prior Publication Data

US 2005/0117151 A1 Jun. 2, 2005

(30) Foreign Application Priority Data

Nov. 28, 2003 (KR) .................. 10-2003-0085825

(51) Int. Cl.
  *G01J 3/40* (2006.01)
  *G06F 15/00* (2006.01)
(52) U.S. Cl. .................. 356/302; 702/189; 702/196
(58) Field of Classification Search ............. 356/302; 702/189, 196
See application file for complete search history.

(56) References Cited

U.S. PATENT DOCUMENTS

| 3,828,173 | A | 8/1974 | Knepler ............ 235/151.35 |
| 4,037,970 | A | 7/1977 | Webster et al. ............ 356/188 |
| 4,648,051 | A | 3/1987 | Wandell et al. |
| 6,535,278 | B1 | 3/2003 | Imura |
| 6,615,162 | B2* | 9/2003 | Bar-Or ............ 702/191 |
| 6,897,953 | B2 | 5/2005 | Watanabe et al. |

FOREIGN PATENT DOCUMENTS

| JP | 61-269463 | 11/1986 |
| JP | 2001-349833 | 12/2001 |

* cited by examiner

*Primary Examiner*—Gregory J. Toatley, Jr.
*Assistant Examiner*—Bryan Giglio
(74) *Attorney, Agent, or Firm*—Lee & Morse, P.C.

(57) ABSTRACT

An analyzing method and system includes projecting light onto a specimen, detecting an optical spectrum from the specimen, dividing the detected optical spectrum by a predetermined time interval, applying a weighting vector and a gain and offset vector to the divided spectra to generate a resolution vector, quantizing an analog signal of the resolution vector to a digital signal, and applying a synthesis vector to the quantized spectra to restore the quantized spectra to a size of the optical spectrum. A spectrum having a large amplitude difference is temporally divided and is analyzed by applying different resolutions to individual time intervals. Spectral portions of the spectrum having relatively small peak amplitudes are selected as a region of interest (ROI) to be modified.

18 Claims, 6 Drawing Sheets

OPTICAL ANALYZER FOR IMPROVING RESOLUTION OF A TIME-VARYING SPECTRUM AND METHOD THEREFOR

BACKGROUND OF THE INVENTION

1. Field of the Invention

The present invention relates to a spectroscopic analyzing apparatus and method. More particularly, the present invention relates to a method and apparatus for improving a resolution of a time-varying spectrum.

2. Description of the Related Art

In a spectroscopic analyzing method, light is projected onto a specimen and a reference material, respectively. The respective detected spectrum amplitudes are compared, and the components of the specimen are analyzed. In reviewing an entire spectral band of a specimen, a main component of the specimen has a meaningful spectrum, which is isolated from the remaining components. By analyzing the amplitude of this meaningful spectrum, the components of the specimen and the content of each of the components can be estimated.

One conventional spectroscopic analyzing method uses infrared radiation from a lamp passing through selected filters so that a specific frequency of radiation is incident upon a sample. A photocell detects the reflected signals, and the detected signals are amplified and output through an amplifier. A gain error of the amplifier is compensated for with a sample and hold circuit. However, each channel has its own corresponding sample and hold circuit. Thus, as the number of channels increases, fabrication cost of the spectral analysis system increases.

In another conventional spectroscopic analyzing method, a spectrum is detected using a plurality of amplifiers. The plurality of amplifiers complicates the system, and the addition of channels causes the overall operating costs to be increased. Also, since each of the plurality of amplifiers has a gain error, the accuracy of the analysis is reduced.

If the spectral amplitude of a specimen being analyzed has a constant size, a spectrum may be readily analyzed by amplifying an optical signal. However, if the spectral amplitudes of the specimen vary across the spectrum, the signal-to-noise ratio (SNR) may not be sufficiently high to analyze the entire spectrum. Accordingly, analysis of that specimen component should be abandoned or another wavelength should be selected.

Hence, it is difficult to spectroscopically analyze detected spectra when the detected spectra have large amplitude differences across the spectra, a method for adaptively enhancing the resolution of the spectra to allow the spectra to be easily analyzed is required.

SUMMARY OF THE INVENTION

The present invention is therefore directed to a spectroscopic analyzing method and apparatus, which substantially overcome one or more of the problems due to the limitations and disadvantages of the related art.

It is a feature of an embodiment of the present invention to provide a spectroscopic analyzing apparatus that enhances the resolution of a spectrum.

It is another feature of an embodiment of the present invention to provide a spectroscopic analyzing method that adaptively enhances the resolution of a spectrum.

It is still another feature of an embodiment of the present invention to enhance resolution, preciseness and SNR in a spectral region of interest (ROI).

It is yet another feature of an embodiment of the present invention to provide a system that is small and inexpensive even when a number of the spectral ROIs is large.

It is still another feature of an embodiment of the present invention to reduce the measurement time of the spectrum, thereby reducing noise influence due to drift.

At least one of the above and other features and advantages of an embodiment of the present invention may be realized by providing a method of analyzing a spectroscopic component, the method including projecting light onto a specimen, detecting an optical spectrum from the specimen, temporally dividing the detected spectrum to form a plurality of spectra, applying a weighting vector and a gain and offset vector to each of the plurality of spectra to generate a resolution vector, quantizing the resolution vector to obtain a digital signal, and applying a synthesis vector to the quantized spectra to restore each quantized spectra to an original form of a corresponding spectra.

The weighting vector may select a spectral ROI (region of interest) to increase resolution in a corresponding spectrum of the plurality of spectra obtained by dividing. The gain and offset vector may amplify the corresponding spectrum of the ROI to adjust a peak amplitude of the corresponding spectrum into a dynamic active region.

At least one of the above and other features and advantages of an embodiment of the present invention may be realized by providing a method for analyzing a spectroscopic component, the method including projecting light onto a specimen, detecting an optical spectrum from the specimen, temporally dividing the detected spectrum into a plurality of spectra, generating a weighting vector representing a region of interest (ROI) from the divided spectra, generating a gain and offset vector for amplifying an original form of each spectra of the ROI, generating a synthesis vector for restoring the divided spectra to the original form thereof, multiplying the weighting vector by the optical spectrum to generate an ROI vector, multiplying the gain and offset vector by the ROI vector to generate a resolution vector, multiplying the resolution vector by the synthesis vector to generate a restoring vector, and adding the restoring vectors to obtain a spectrum of the original form having enhanced resolution.

The gain and offset vector may amplify the corresponding spectrum of the ROI to adjust a peak amplitude of the corresponding spectrum into a dynamic active region.

At least one of the above and other features and advantages of an embodiment of the present invention may be realized by providing a spectroscopic analyzer, including a light source, a specimen, a detector which detects an optical spectrum generated by projecting light from the light source to the specimen, a spectral weighting block which adjusts a weighting vector and a gain and offset vector with respect to a region of interest (ROI) of the optical spectrum, an up-down resolution block which amplifies the optical spectrum detected by the detector to generate a resolution vector in accordance with the weighting vector and the gain and offset vector, an analog-to-digital converter which receives the resolution vector output from the up-down resolution block, and converts the received resolution vector to a digital signal, and a spectrum synthesis block which multiplies an output of the analog-digital converter by a synthesis vector for restoring the optical spectrum to an original form to generate a restoring vector and adding the restoring vector to the output of the analog-digital converter to output a spectrum having the original form and enhanced resolution.

The weighting vector may select a region having a relatively small amplitude, and, thus, a relatively low resolution, in the optical spectra divided by a predetermined time interval as the ROI. The gain and offset vector may amplify the corresponding spectrum of the ROI to adjust a peak amplitude of the corresponding spectrum into a dynamic active region. The up-down resolution block may include a gain control unit which receives the gain vector from the spectral weighting block, an offset control unit which receives the offset vector from the spectral weighting block, and an amplifying unit which amplifies the spectrum of the ROI in accordance with the gain vector and the offset vector.

According to an embodiment of the inventive spectroscopic analyzing method and apparatus, a spectrum having a large amplitude difference is divided by a time interval and is analyzed by differentially applying the resolution by the time interval. Accordingly, the resolution, preciseness and SNR of the spectral ROI are enhanced.

Also, when the number of the ROIs is large, the related art spectroscopic analyzer causes the system construction thereof to be large and to be expensive, while an embodiment of the inventive analyzer allows the system construction thereof to be small and inexpensive.

Further, since an embodiment of the inventive analyzing method decreases the measurement time of the spectrum, noise influence due to drift is reduced compared with the related art analyzing method.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 2003-85825, filed on Nov. 28, 2003, in the Korean Intellectual Property Office, and entitled: "Optical Analyzer for Improving Resolution of Time-varying Spectrum and Device Therefor," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Figure 1:
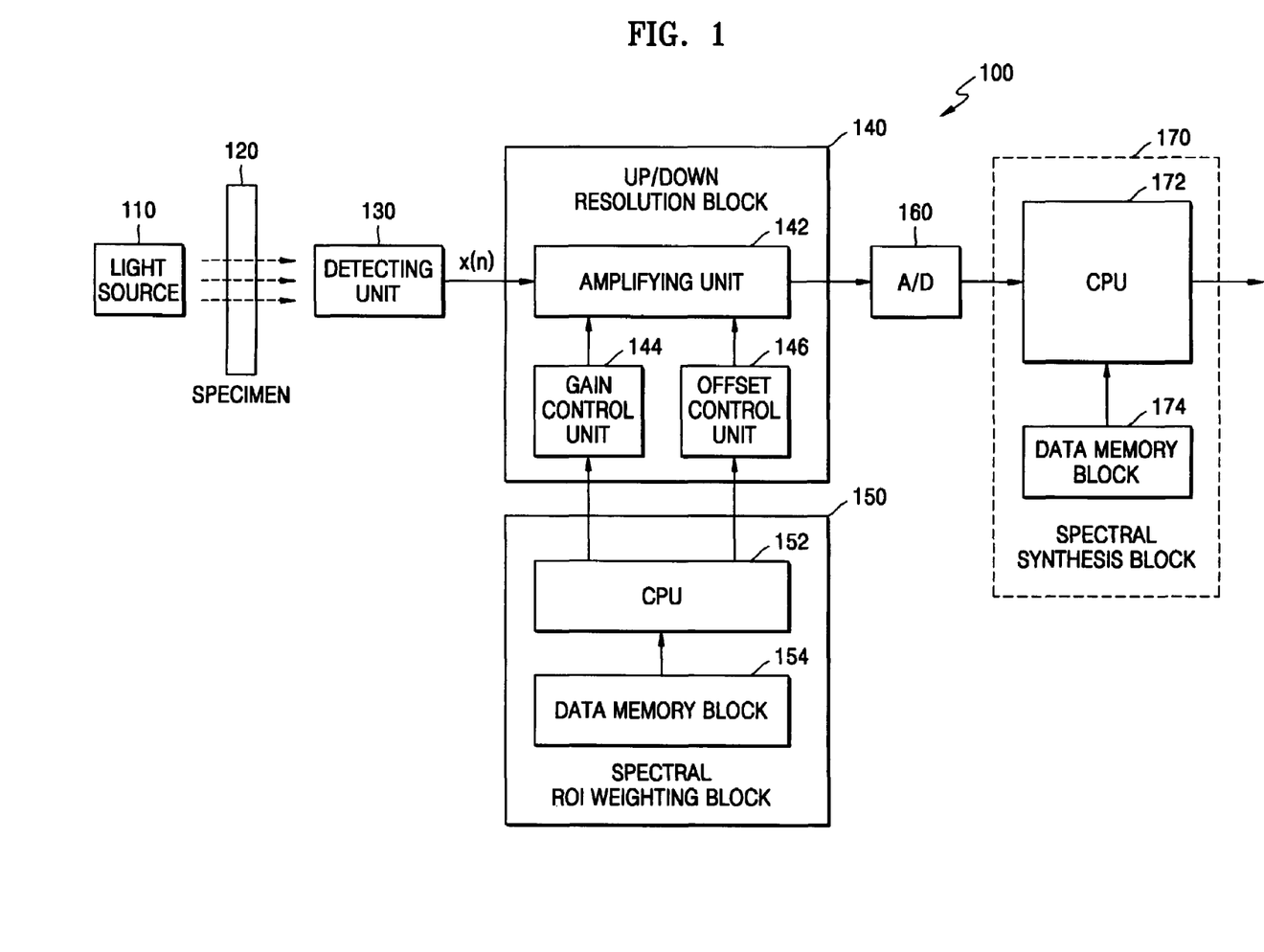
FIG. 1 illustrates a block diagram of a spectroscopic analyzing apparatus according to an embodiment of the present invention.

FIG. 1 illustrates a block diagram of a spectroscopic analyzing apparatus according to an embodiment of the present invention. Referring to FIG. 1, a spectroscopic analyzer 100 includes a light source 110, a specimen 120, a detecting unit 130, an up/down resolution block 140, a spectral region of interest (ROI) weighting block 150, an analog-to-digital (A/D) converter 160, and a spectral synthesis block 170.

Light emitted from the light source 110 passes through the specimen 120 and is transmitted to the detecting unit 130. The detecting unit 130 converts an optical signal into an electrical signal. Electrical signals are generally expressed as a variation of voltage, and the voltage variation with respect to time is referred to as a spectrum signal. Since the voltage variation detected by the detecting unit 140 is small, the spectrum signal is modified by the up/down resolution block 140.

The up/down resolution block 140 includes an amplifying unit 142, a gain control unit 144, and an offset control unit 146. The amplifying unit 142 amplifies an output spectrum signal x(n) of the detecting unit 130 and adjusts the size of the amplified signal to be matched with a dynamic active region, i.e., such that the signal can be stably amplified. The spectrum signal amplified by the amplifying unit 142 can be divided by a time interval depending on time or by a predetermined time interval. The spectra obtained by dividing the spectrum into time intervals can be amplified by the amplifying unit 142 by different values, i.e., by a gain value and an offset value that are control signals provided by the gain control unit 144 and the offset control unit 146.

The control signals of the gain control unit 144 and the offset control unit 146 are provided from the spectral ROI weighting block 150. The spectral ROI weighting block 150 includes a CPU 152 and a data memory block 154. The data memory block 154 stores gain and offset values relative to positions in the waveform, which are read by the CPU 152 and output to the respective gain control unit 144 and the offset control unit 146. The spectral ROI weighting block 150 selects a spectral wavelength band to be used for the analysis of the specimen on the spectrum of the specimen 120 and divides the spectrum depending on time according to the selected wavelength band. A spectral portion in the divided wavelength band having a relatively low peak amplitude, e.g., lower than the dynamic range in other wavelengths bands, is selected as a spectral portion to receive additional amplification, thereby increasing the resolution within this spectral portion. More than one portion of the spectrum may be selected. The spectral portion having increased resolution is determined by a weighting vector generated in the spectral ROI weighting block 150. This weighting vector is provided to the gain control unit 144 and the offset control unit 146.

The A/D converter 160 quantizes the amplified spectrum to convert it into a digital signal and transfers the quantized digital signal to the spectral synthesis block 170. The spectral synthesis block 170 includes a CPU 172 and a data memory block 174. The position in the waveform at which different amplification parameters are to be used remains the same for the reverse conversion performed by the spectral synthesis block 170. This position, as well as the reverse conversion information for the gain and offset values, is stored in the data memory block 174. The spectral synthesis block 170 synthesizes the spectrum having a resolution applied differentially depending on a time interval in the up/down resolution block 140 to an original shaped spectrum. The functions of the spectral ROI weighting block 150 and the spectral synthesis block 170 may be performed by the same CPU and data memory block.

Hereinafter, a method of decomposing a spectrum of a ROI by applying the vectors obtained in the flow chart of FIG. 2 to the block diagram of FIG. 3 so as to enhance the resolution of the spectrum will be described in detail.

Figure 2:
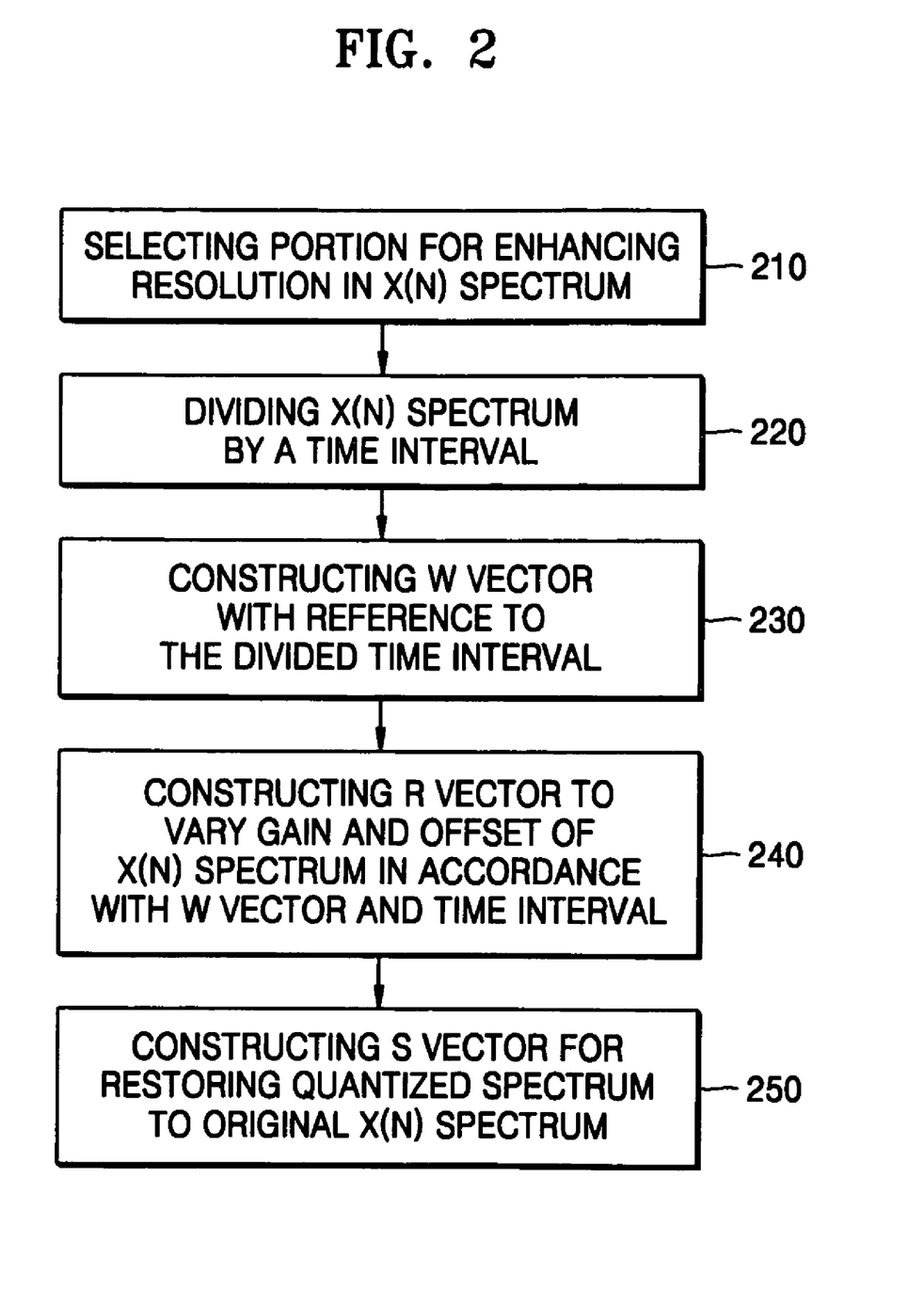
FIG. 2 is a flow chart of a generation sequence of vectors applied to the spectroscopic analyzing apparatus of FIG. 1.

As shown in FIG. 2, from the original spectrum x(n) received from the detecting unit (see 130 of FIG. 1), a spectral portion to receive enhanced resolution is selected in step 210. The original spectrum x(n) is divided by a time interval at step 220. A weighting vector W is constructed with reference to the divided time interval at step 230. A vector R which varies the gain and offset of the x(n) spectrum depending on the weighting vector W and the time interval is constructed at step 240. For example, the offset adjustment may be selected to ensure that an amplified spectrum remains within the dynamic active region. Also, a vector S for restoring the divided spectrum to the original size spectrum is constructed at step 250.

Figure 3:
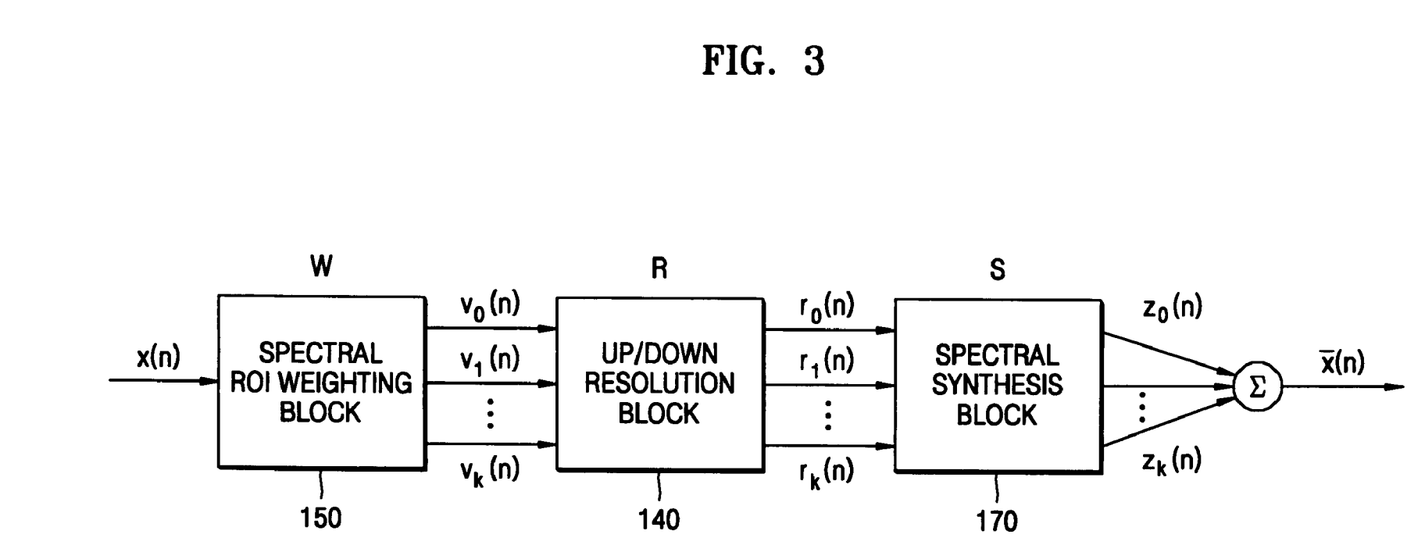
FIG. 3 illustrates a more specific block diagram of a flow of the vectors in the spectroscopic analyzing apparatus of FIG. 1.

Referring to FIG. 3, the spectral ROI weighting block 150 multiplies the weighting vector W with the original spectrum x(n) received from the detecting unit (see 130 of FIG. 1) to thereby generate an ROI vector v(n). An example of the weighting vector W is shown in Equation (1) below:

$$W = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix} \quad (1)$$

The ROI vector v(n) is expressed by Equation (2) below:

$$v(n) = \begin{bmatrix} v_0(n) \\ v_1(n) \\ v_2(n) \\ \vdots \\ v_k(n) \end{bmatrix} \quad (2)$$

Figure 4:
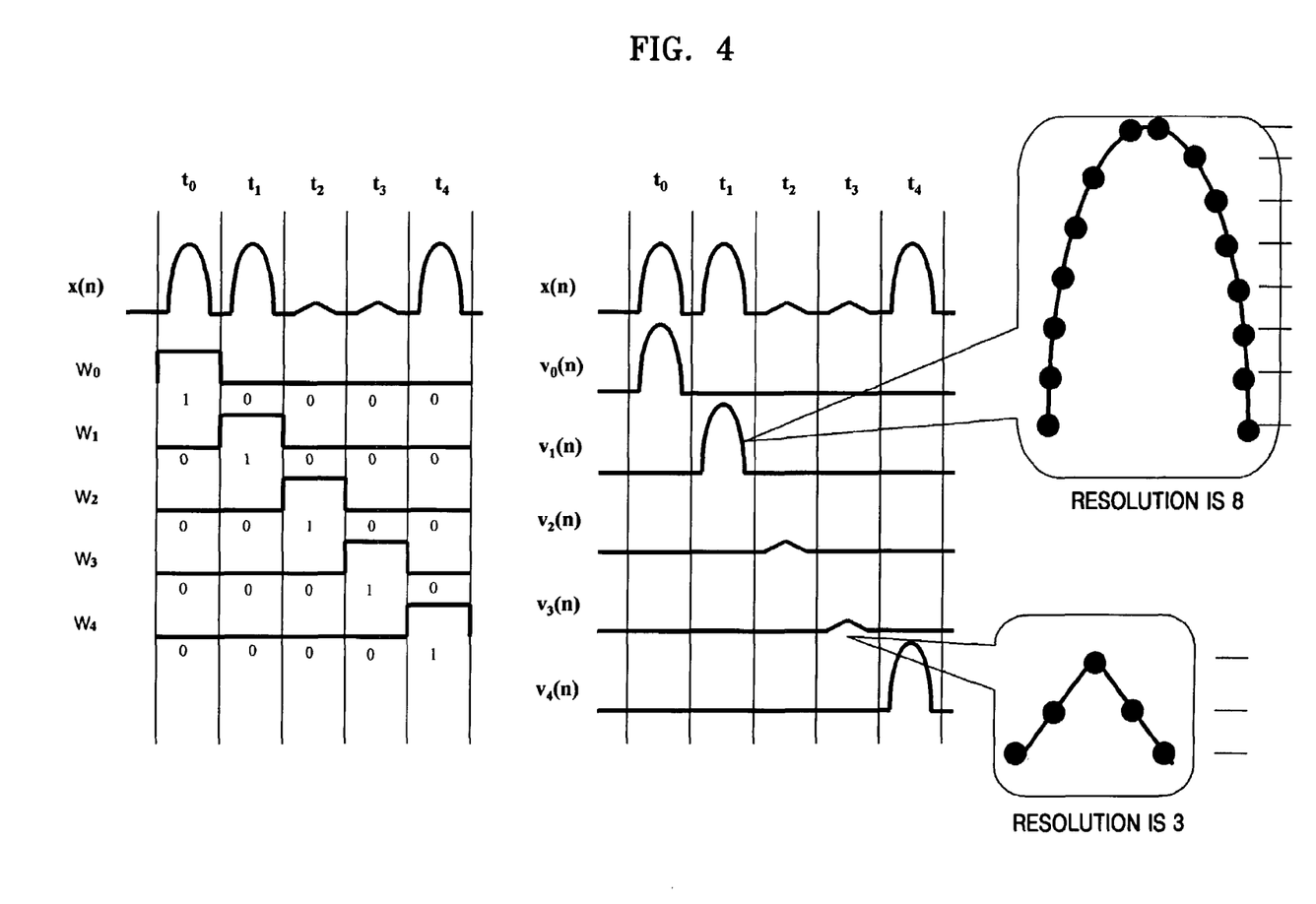
FIGS. 4 and 5 illustrate an original spectrum detected in a specimen and a resolution-enhanced spectrum, respectively.

FIG. 4 illustrates the weighting vector W and the ROI vector v(n) with respect to the original spectrum x(n). While the resolution of the second ROI vector $v_1(n)$ allows eight gradations to be determined, the resolution of the fourth ROI vector $v_3(n)$ only allows three gradations to be determined.

This discrepancy arises because a peak of the fourth ROI vector $v_3(n)$ is smaller than that of the second ROI vector $v_1(n)$.

Again returning to FIG. 3, the up/down resolution block 140 receives the ROI vector v(n) and generates a resolution vector r(n) by performing a predetermined functional product of the received ROI vector v(n) and the gain and offset vector R having a gain component H and an offset component G. The gain and offset vector R is defined by Equation (3) below:

$$R = \begin{bmatrix} H_0 & G_0 \\ H_1 & G_1 \\ \vdots & \vdots \\ H_k & G_k \end{bmatrix} \quad (3)$$

The resolution vector r(n) can be expressed by the functional product of the ROI vector v(n) and the gain and offset vector R by Equation (4) below:

$$F[R, v(n)] = H \cdot v(n) + G = r(n) \quad (4)$$

Accordingly, $$F[R_0, v_0(n)] = H_0 \cdot v_0(n) + G_0 = r_0(n)$$

$$F[R_1, v_1(n)] = H_1 \cdot v_1(n) + G_1 = r_1(n)$$

$$F[R_2, v_2(n)] = H_2 \cdot v_2(n) + G_2 = r_2(n)$$

$$\cdots$$

$$F[R_k, v_k(n)] = H_k \cdot v_k(n) + G_k = r_k(n).$$

The functional product of the resolution vector r(n) and the synthesis vector S for restoring a quantized vector to the size of the original vector x(n) is performed to generate a restoring vector z(n). Herein, the synthesis vector S is defined by Equation (5) below:

$$S = \begin{bmatrix} \frac{1}{H_0} & -\frac{G_0}{H_0} \\ \frac{1}{H_1} & -\frac{G_1}{H_1} \\ \frac{1}{H_2} & -\frac{G_2}{H_2} \\ \vdots & \vdots \\ \frac{1}{H_k} & -\frac{G_k}{H_k} \end{bmatrix} \quad (5)$$

The restoring vector z(n) can be expressed by a functional product of the synthesis vector S and the resolution vector r(n) by Equation (6) below:

$$F[S, r(n)] = \frac{1}{H} r(n) - \frac{G}{H} = z(n) \quad (6)$$

Accordingly, $$F[S_0, r_0(n)] = \frac{1}{H_0} r_0(n) - \frac{G_0}{H_0} = z_0(n)$$

$$F[S_1, r_1(n)] = \frac{1}{H_1} r_1(n) - \frac{G_1}{H_1} = z_1(n)$$

$$F[S_2, r_2(n)] = \frac{1}{H_2} r_2(n) - \frac{G_2}{H_2} = z_2(n)$$

$$\cdots$$

$$F[S_k, r_k(n)] = \frac{1}{H_k} r_k(n) - \frac{G_k}{H_k} = z_k(n).$$

A restored spectrum $\bar{x}(n)$ including a spectral portion with enhanced resolution is obtained by combining the spectral portions of z(n), as indicated in FIG. 3. The restored spectrum again has the amplitude and shape, i.e., form, of the original spectrum x(n).

Figure 5:
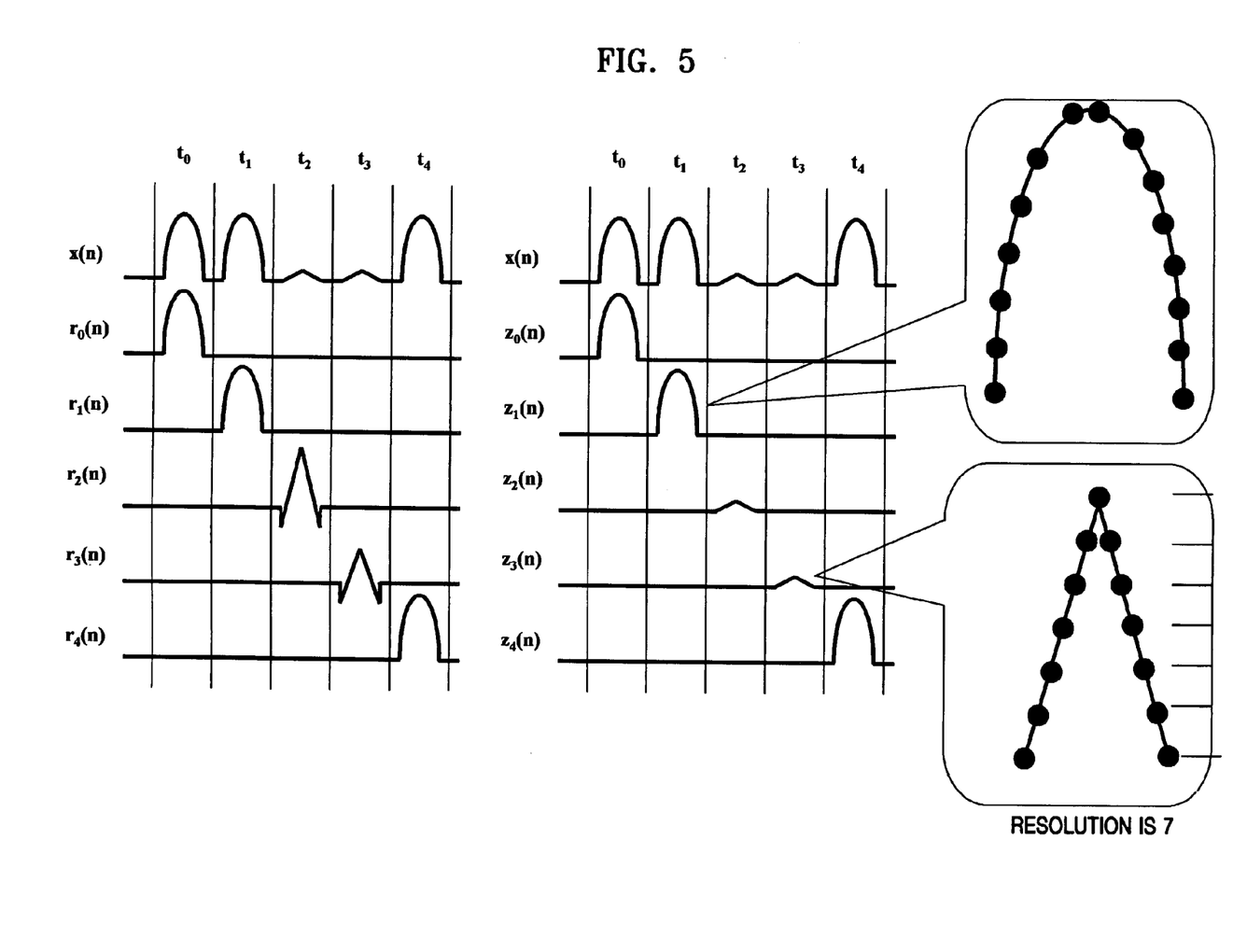

FIG. 5 shows the resolution vector r(n) and the restoring vector z(n) with respect to the original spectrum x(n). In FIG. 5, the resolution of the fourth ROI vector $v_3(n)$, which only allowed three gradations in FIG. 4, is enhanced to allow seven gradations. In the particular example shown in FIG. 5, the gain and offset vector R may be given by:

$$R = \begin{bmatrix} 1 & 0 \\ 1 & 0 \\ 5 & 3 \\ 4 & 4 \\ 1 & 0 \end{bmatrix}.$$

Thus, where resolution is already satisfactory, the spectra remain the same, while in ROIs where the resolution needs to be improved, the spectra are appropriately amplified and shifted within the dynamic active region.

Figure 6:
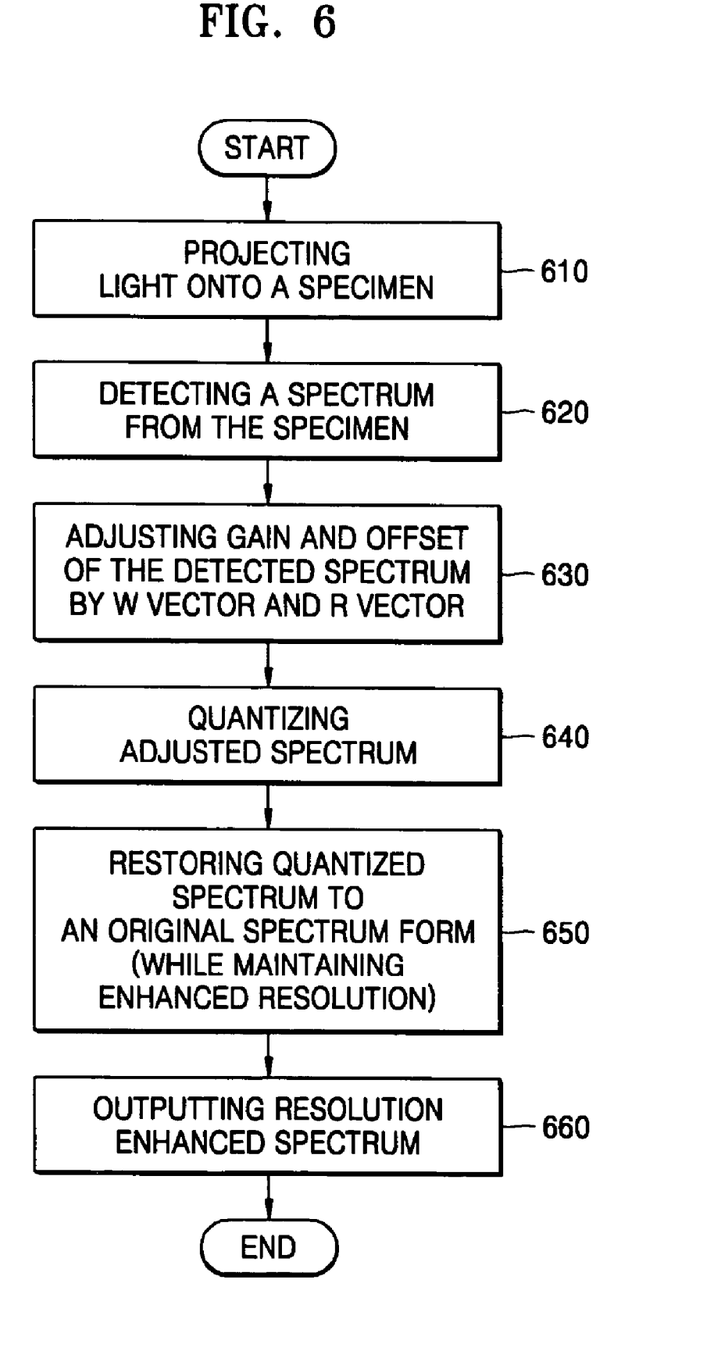
FIG. 6 is a flow chart of an operation of a spectroscopic analyzing method according to an embodiment of the present invention.

A method for enhancing the resolution of the spectrum by a time interval using the spectroscopic analyzer 100 can be summarized as shown in FIG. 6. Light from the light source 110 is projected onto the specimen 120 at step 610. Light from the specimen 120 is detected by the detecting unit 130 at step 620, which outputs a spectrum. The spectrum is temporally divided into a plurality of spectra at step 630 in accordance with the weighting vector W. Also, the gain and offset of each spectra is adjusted in the up/down resolution block 140 in accordance with the gain and offset vector R and the weighting vector W in step 630 to form a resolution vector, with a resolution component for each spectra. The resolution vector is quantized by the A/D converter 160 at step 640. Then, the quantized spectra, having an enhanced resolution, are synthesized to form restoring spectra having enhanced resolution and the original form at step 650. Thus, the enhanced resolution of the restored spectra is maintained. The resolution enhanced spectrum is formed by combining the restored spectra at step 660.

While the present invention has been particularly shown and described with reference to exemplary embodiments thereof, it will be understood by those of ordinary skill in the art that various changes in form and details may be made therein without departing from the spirit and scope of the present invention as defined by the following claims. For example, while the above discussion has assumed the transmitted light from the sample is being examined, the same principles of increasing the resolution may be used when examining reflected spectra. Also, while CPUs were illustrated, any appropriate processor may be used.

What is claimed is:

1. A method of analyzing a spectroscopic component, the method comprising:
projecting light onto a specimen;
detecting an optical spectrum from the specimen;
temporally dividing the detected spectrum to form a plurality of spectra;
applying a weighting vector and a gain and offset vector to each of the plurality of spectra to generate a resolution vector;
quantizing the resolution vector to obtain a digital signal;
applying a synthesis vector to the quantized spectra to restore each quantized spectrum to an original form of a corresponding original spectrum; and
outputting a spectrum having the original form and enhanced resolution.

2. The method as claimed in claim 1, wherein the weighting vector selects a spectral ROI (region of interest) to increase resolution in a corresponding spectrum of the plurality of spectra obtained by dividing.

3. The method as claimed in claim 2, wherein the gain and offset vector amplifies the corresponding spectrum of the ROI to adjust a peak amplitude of the corresponding spectrum into a dynamic active region.

4. The method as claimed in claim 1, wherein the resolution vector is expressed by $r(n)=F[R,v(n)]=H \cdot v(n)+G$, in which the gain and offset vector R is expressed by $$R = \begin{bmatrix} H_0 & G_0 \\ H_1 & G_1 \\ \vdots & \vdots \\ H_k & G_k \end{bmatrix},$$

where H is the gain and G is the offset.

5. The method as claimed in claim 1, wherein the synthesis vector S is expressed by $$S = \begin{bmatrix} \frac{1}{H_0} & -\frac{G_0}{H_0} \\ \frac{1}{H_1} & -\frac{G_1}{H_1} \\ \frac{1}{H_2} & -\frac{G_2}{H_2} \\ \vdots & \vdots \\ \frac{1}{H_k} & -\frac{G_k}{H_k} \end{bmatrix},$$

where H is the gain and G is the offset.

6. The method as claimed in claim 1, wherein the weighting vector is expressed by $$W = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix}.$$

7. A method for analyzing a spectroscopic component, the method comprising:
projecting light onto a specimen;
detecting an optical spectrum from the specimen;
temporally dividing the detected spectrum into a plurality of spectra;
generating a weighting vector representing a region of interest (ROI) from the divided spectra;
generating a gain and offset vector for amplifying an original form of each spectrum of the ROI;
generating a synthesis vector for restoring the divided spectra to the original form thereof;
multiplying the weighting vector by the optical spectrum to generate an ROI vector;
multiplying the gain and offset vector by the ROI vector to generate a resolution vector;
multiplying the resolution vector by the synthesis vector to generate a restoring vector;
adding the restoring vectors to obtain a spectrum of the original form having enhanced resolution; and
outputting a spectrum having the original form and enhanced resolution.

8. The method as claimed in claim 7, wherein the gain and offset vector amplifies the corresponding spectrum of the ROI to adjust a peak amplitude of the corresponding spectrum into a dynamic active region.

9. The method as claimed in claim 7, wherein the weighting vector is expressed by $$W = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix}.$$

10. The method as claimed in claim 7, wherein the resolution vector is expressed by $r(n)=F[R,v(n)]=H\cdot v(n)+G$, in which the gain and offset vector R is expressed by $$R = \begin{bmatrix} H_0 & G_0 \\ H_1 & G_1 \\ \vdots & \vdots \\ H_k & G_k \end{bmatrix},$$

where G is the gain and H is the offset.

11. The method as claimed in claim 7, wherein the synthesis vector S is expressed by $$S = \begin{bmatrix} \frac{1}{H_0} & -\frac{G_0}{H_0} \\ \frac{1}{H_1} & -\frac{G_1}{H_1} \\ \frac{1}{H_2} & -\frac{G_2}{H_2} \\ \vdots & \vdots \\ \frac{1}{H_k} & -\frac{G_k}{H_k} \end{bmatrix},$$

where H is the gain and G is the offset.

12. A spectroscopic analyzer, comprising:
a light source;
a specimen;
a detector which detects an optical spectrum generated by projecting light from the light source to the specimen;
a spectral weighting block which adjusts a weighting vector and a gain and offset vector with respect to a region of interest (ROI) of the optical spectrum;
an up-down resolution block which amplifies the optical spectrum detected by the detector to generate a resolution vector in accordance with the weighting vector and the gain and offset vector;
an analog-to-digital converter which receives the resolution vector output from the up-down resolution block, and converts the received resolution vector to a digital signal; and
a spectrum synthesis block which multiplies an output of the analog-digital converter by a synthesis vector for restoring the optical spectrum to an original form to generate a restoring vector and adding the restoring vector to the output of the analog-digital converter to output a spectrum having the original form and enhanced resolution.

13. The spectroscopic analyzer as claimed in claim 12, wherein the weighting vector selects a region having a relatively small amplitude, and, thus, a relatively low resolution, in the optical spectra divided by a predetermined time interval as the ROI.

14. The spectroscopic analyzer as claimed in claim 12, wherein the gain and offset vector amplifies the corresponding spectrum of the ROI to adjust a peak amplitude of the corresponding spectrum into a dynamic active region.

15. The spectroscopic analyzer as claimed in claim 12, wherein the up-down resolution block comprises:
a gain control unit which receives the gain vector from the spectral weighting block;
an offset control unit which receives the offset vector from the spectral weighting block; and
an amplifying unit which amplifies the spectrum of the ROI in accordance with the gain vector and the offset vector.

16. The spectroscopic analyzer as claimed in claim 12, wherein the weighting vector is expressed by $$W = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix}.$$

17. The spectroscopic analyzer as claimed in claim 12, wherein the resolution vector is expressed by $r(n)=F[R,v(n)]=H\cdot v(n)+G$, in which the gain and offset vector R is expressed by $$R = \begin{bmatrix} H_0 & G_0 \\ H_1 & G_1 \\ \vdots & \vdots \\ H_k & G_k \end{bmatrix},$$

where H is the gain and G is the offset.

18. The spectroscopic analyzer as claimed in claim 12, wherein the synthesis vector S is expressed by $$S = \begin{bmatrix} \frac{1}{H_0} & -\frac{G_0}{H_0} \\ \frac{1}{H_1} & -\frac{G_1}{H_1} \\ \frac{1}{H_2} & -\frac{G_2}{H_2} \\ \vdots & \vdots \\ \frac{1}{H_k} & -\frac{G_k}{H_k} \end{bmatrix},$$

where H is the gain and G is the offset.

* * * * *